(12) United States Patent
Hoskinson et al.

(10) Patent No.: US 6,497,153 B1
(45) Date of Patent: Dec. 24, 2002

(54) MEASURING SPATIAL VARIABILITY IN SOIL CHARACTERISTICS

(75) Inventors: Reed L. Hoskinson, Rigby, ID (US); John M. Svoboda, Idaho Falls, ID (US); J. Wayne Sawyer, Hampton, VA (US); John R. Hess, Ashton, ID (US); J. Richard Hess, Idaho Falls, ID (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 0 days.

(21) Appl. No.: 09/677,183

(22) Filed: Sep. 28, 2000

(51) Int. Cl.[7] .................................................. G01B 5/00
(52) U.S. Cl. ........................................................ 73/784
(58) Field of Search ........................ 73/781, 784, 763, 73/767; 56/10.2 A

(56) References Cited

U.S. PATENT DOCUMENTS 4,437,048 A * 3/1984 Arnold ....................... 318/663
4,454,919 A * 6/1984 Arnold et al. .................. 172/1
4,878,543 A * 11/1989 Kauss ............................ 172/2
6,041,582 A * 3/2000 Tiede et al. ................... 56/10.2

* cited by examiner

Primary Examiner—Max Noori
(74) Attorney, Agent, or Firm—Workman Nydegger & Seeley

(57) ABSTRACT

The present invention provides systems and methods for measuring a load force associated with pulling a farm implement through soil that is used to generate a spatially variable map that represents the spatial variability of the physical characteristics of the soil. An instrumented hitch pin configured to measure a load force is provided that measures the load force generated by a farm implement when the farm implement is connected with a tractor and pulled through or across soil. Each time a load force is measured, a global positioning system identifies the location of the measurement. This data is stored and analyzed to generate a spatially variable map of the soil. This map is representative of the physical characteristics of the soil, which are inferred from the magnitude of the load force.

28 Claims, 2 Drawing Sheets

MEASURING SPATIAL VARIABILITY IN SOIL CHARACTERISTICS

CONTRACTUAL ORIGIN OF THE INVENTION

This invention was made with United States Government support under Contract No. DE-AC07-94ID13223, now Contract No. DE-AC07-99ID13727 awarded by the United States Department of Energy. The United States Government has certain rights in the invention.

BACKGROUND OF THE INVENTION

1. Field of the Invention

The present invention relates to systems and methods for measuring the physical characteristics of soil. More particularly, the present invention relates to systems and methods for collecting data representing the spatial variability of the physical characteristics of soil for use in precision farming.

2. Present State of the Art

Precision farming is intended to enable farmers to optimize their operations such that crop yields are maximized. There are many different factors that have a bearing on crop yield including the amount and type of fertilizer applied to the crops, the amount and type of pesticides and herbicides applied to the crops, the amount of irrigation that the crop receives, the machinery used to cultivate and grow the crop, expenses incurred to produce the crop and the like.

In particular, the physical condition of the soil can have a significant effect on the crop yield in both an agricultural and a financial sense. Agriculturally, the physical condition of the soil is related to environmental problems such as erosion, contaminated water runoff, over-watering, excessive use of fertilizers and pesticides, over-tilling, and the like. Thus, an understanding of the physical characteristics of the soil can assist in determining how agricultural factors, such as fertilizer or water, may be spatially varied such that the resources are utilized more efficiently.

Financially, it is costly to obtain a map of the physical characteristics of the soil in a field. Conventional methods include physically collecting soil samples that are sent to a lab for analysis. Unfortunately, samples taken in this manner each represent relatively large areas. Often, a single soil sample is taken for every one to four acres and because soil conditions can vary widely over short distances, this method only provides a crude map of the physical characteristics of the soil in addition to being costly.

Another sampling method requires machinery that is explicitly designed to sense the conditions of the soil. This method requires the farmer to traverse the field an extra and unnecessary time with the special machinery such that the physical conditions may be measured. Traversing a field in this manner is expensive to the farmer and results in data that is still relatively crude. More specifically, these methods are costly, time-consuming and only provide limited data concerning the physical characteristics of the soil.

Precision farmers have come to realize, however, that an understanding of the physical characteristics of the soil can be used to reduce the expense incurred to cultivate the crop as well as increase the crop yield. The problem is being able to obtain an accurate measurement of those characteristics without increasing cost or otherwise interfering with crop development and growth. An understanding of the physical characteristics of the soil is particularly useful in "no-till" farming. No-till farming is environmentally preferred for several reasons. Erosion can be reduced, fertilizer usage can be optimized, irrigation can be more effectively monitored, and the like.

The physical condition of the soil is therefore an important aspect of no-till farming operations. One of the problems associated with no-till farming, for example, is that the physical characteristics and crop residue that may be encountered near the surface of the soil can vary considerably. This variability has a direct effect on the condition of the furrows as well as on the depth that a seed is planted. In particular, wheel traffic can result in more dense soil. The density of the soil can have an affect on many aspects of farming. For example, when a particular crop is planted, it is often desirable to control the depth at which the seeds are placed in the soil. One of the problems associated with no-till farming is that the planter settings are typically fixed for the average condition of the soil and the planter will not perform optimally when other soil conditions are encountered. As a result, the crop yield is not maximized because the planting conditions are not optimized.

However, there is no affordable tool or system that is capable of sufficiently gathering information about the physical characteristics of soil. In order to effectively monitor or implement the physical characteristics into precision farming, it is necessary to have more specific data about the physical characteristics of the soil. What is needed are practical and cost effective systems and methods for better understanding and measuring the spatial variability of the physical conditions of soil. Understanding and managing the variability in soil conditions will also enable other aspects of precision farming to be improved and optimized.

SUMMARY OF THE INVENTION

The present invention relates to systems and methods for measuring the physical characteristics of soil. Accurate measurements of soil's physical characteristics can be used to generate a map that represents the spatial variability of the soil's physical characteristics. Understanding the spatial variability of soil characteristics is useful for precision farming because other agricultural inputs, such as fertilizer and water, can be spatially varied according the spatial variability of the soil. As a result, the crop yield is improved and resources can be used more efficiently. In addition, the expense of obtaining the data representing the spatial variability of the physical characteristics of the soil is minimal because the systems and methods of the present invention are preferably integrated with other farming operations.

The physical characteristics of soil include density and water holding capacity, which can be inferred by measuring the force required to pull or push machinery either through or across the soil. In one embodiment of the present invention, the force required to pull a farm implement, such as a plow, a planter or the like, is continually measured and collected as the field is traversed with the farm implement. As the force measurements are collected and recorded, a positioning system is used to identify and map the locations of each force measurement. The forces associated with the stored locations can be used to produce a spatially variable map that represents the spatial variability of the physical conditions of the soil. The amount of force is indicative of soil conditions such as texture, hardness, water-holding capacity, and the like.

In one embodiment, load sensors are integrated with a hitch pin that secures a draw bar to a tractor or other machinery. The load sensors measure the force against the hitch pin as a tractor pulls farm machinery through or across the ground or soil of a field. The force measured by these load sensors is recorded along with a position provided by a global positioning system. Because a position is associated with each measured force, the spatial variability of the force can be mapped and the physical characteristics of the soil can be inferred and used to support precision farming. Often, the resulting map is used as a factor by a decision support system which takes into account many factors when rendering a decision relating to the crop yield.

In one embodiment, the hitch pin may be incorporated as part of a tractor. The hitch pin may be connected to a draw bar of a tractor or the hitch pin may be incorporated with the three point hitch system of other tractors. The present invention, however, is not limited to agricultural equipment, but can be implemented with other machinery, such as construction machinery, to measure soil characteristics. For example, a grader or bulldozer may utilize the systems and methods of the present to measure the soil characteristics of the applicable surface or soil.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
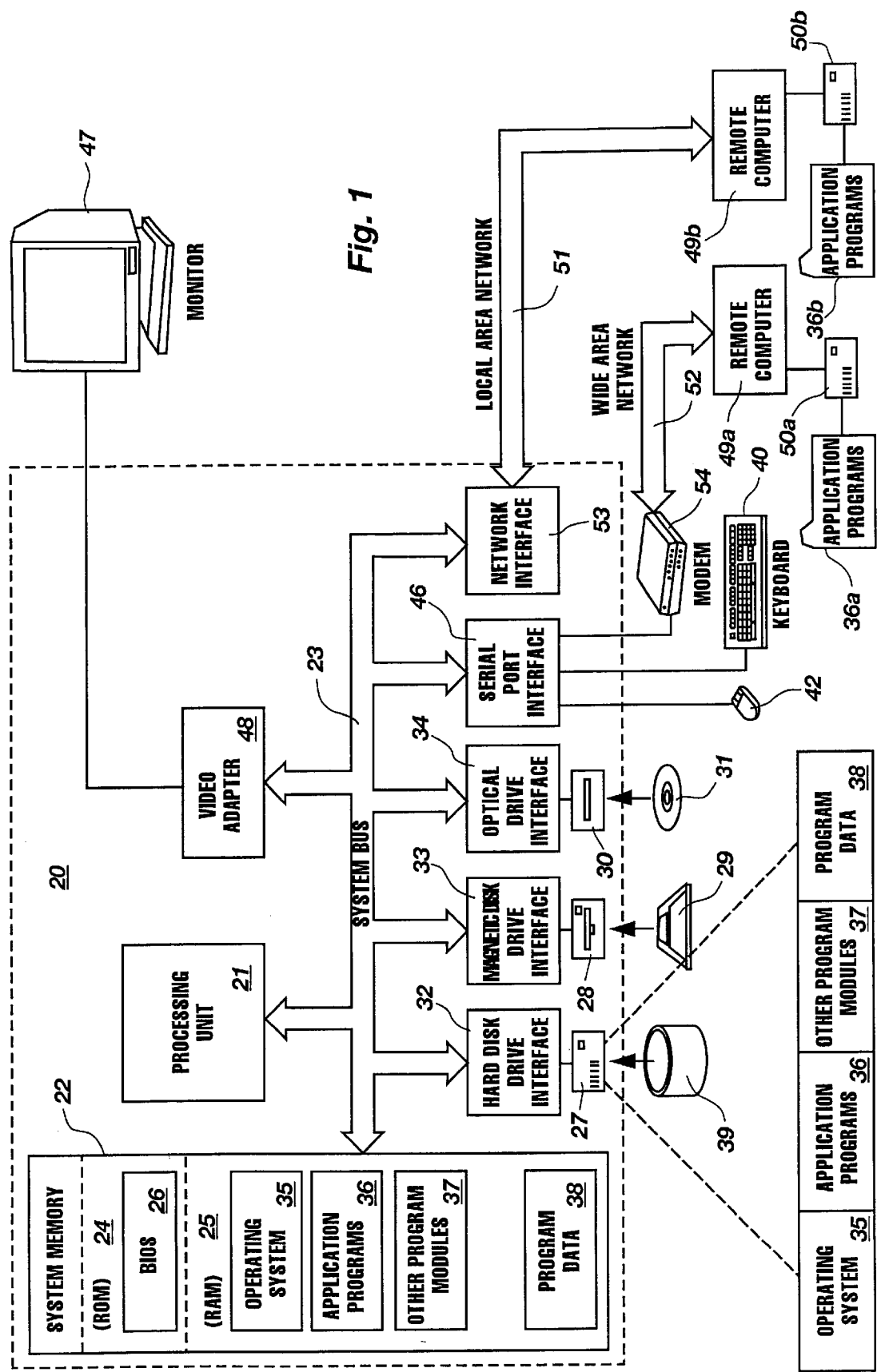
FIG. 1 illustrates an exemplary system for storing and processing the data representing the spatial variability of the soil's physical characteristics.

Measuring the spatial variability of the physical characteristics of soil is an important aspect of generating a map that depicts the spatial variability of the physical characteristics of the soil. In general, the physical characteristics of the soil are inferred by measuring the force required to pull or push machinery along or through the soil. Preferably, the measurements are taken continuously in real time or in short intervals. In conjunction with the force measurement, a positioning system is used to associate a location with every measured force. With this data, a map may be generated that illustrates the spatial variability of the measured force, from which the physical characteristics of the soil such as hardness, density, water-holding capacity, and the like may be inferred or computed.

The present invention provides several advantages. First, the systems and methods of the present invention can be incorporated into new and existing machinery that are used for normal farming operations. For example, the force measurements may be taken while a field is being plowed or planted. This is significant because each time a field is traversed, the cost of farming is increased and energy is expended. Measuring the force while performing another necessary farming activity eliminates the need to traverse the field with equipment that is specifically designed to assess the physical characteristics of the soil. Another benefit of integrating the systems and methods of the present invention with new and existing machinery in this manner is that the collection of data does not require the farmer to incur the expense of obtaining soil samples to obtain information about the physical characteristics of the soil. Rather, the data that represents the physical characteristics of the soil may be collected during the normal course of farm operations.

Another advantage is that the systems and methods of the present invention are cost effective because they can be integrated with existing machinery. In addition, data can be collected repeatedly without incurring additional cost because measurements can be taken with many different farm implements. In other words, data can be collected when the field is plowed, when the field is planted, when the field is harvested and the like. Not only does this ability to perform multiple measurements enhance the data that is collected, but the costs incurred by having independent contractors perform point sampling is also eliminated.

The present invention is also useful in no-till farming applications. Tilling soil is not environmentally friendly because it results in soil erosion, disturbs the soil microecology, requires additional labor and cost, requires more water, and the like when compared to no-till farming. The disadvantage of no-till farming is that it often results in soil compaction that correlates with lower crop yields. By mapping the physical characteristics of the soil in accordance with the present invention, no-till farming can be made more economically viable by identifying those areas of a field where the soil is too compact or dense. As a result, energy and time is expended to till only those areas of a field that require tilling. This should result in less soil compaction and higher crop yields for no-till farming.

Another advantage of the present invention is the ability to collect more data than expensive conventional methods. Soil characteristics can change rapidly across a field and the present invention can collect or log data as often as needed. Typically, data is collected every one to three seconds, which results in a measurement for every six to 10 feet of soil instead of a measurement for every acre or group of acres. In addition, because the present invention can be used with various farm implements, data can be collected for different soil depths. In this manner, a three dimensional portrait of the soil's physical characteristics may be generated. The measurements can be taken in real time, which makes it is possible to make adjustments to the farm implement based on the collected data in real time.

The present invention provides substantially equal resolution and accuracy that is independent of the farm implement that is being pulled or pushed. If the present invention is used in conjunction with a farm implement that provides light resistance, such as a planter, the quality of data is not different from the data collected when a farm implement such as a plow, which provides greater resistance, is used.

The present invention extends both systems and methods for measuring the spatial variability of the physical characteristics of soil. The embodiments of the present invention may comprise a special purpose or general purpose computer including various computer hardware, as discussed in greater detail below.

Embodiments within the scope of the present invention also include computer-readable media for carrying or having computer-executable instructions or data structures stored thereon. Such computer-readable media can be any available media which can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer.

When information is transferred or provided over a network or another communications connection (either hardwired, wireless, or a combination of hardwired or wireless) to a computer, the computer properly views the connection as a computer-readable medium. Thus, any such a connection is properly termed a computer-readable medium. Combinations of the above should also be included within the scope of computer-readable media. Computer-executable instructions comprise, for example, instructions and data which cause a general purpose computer, special purpose computer, or special purpose processing device to perform a certain function or group of functions.

FIG. 1 and the following discussion are intended to provide a brief, general description of a suitable computing environment in which the invention may be implemented. Although not required, the invention will be described in the general context of computer-executable instructions, such as program modules, being executed by computers in network environments. Generally, program modules include routines, programs, objects, components, data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represent examples of corresponding acts for implementing the functions described in such steps.

Those skilled in the art will appreciate that the invention may be practiced in network computing environments with many types of computer system configurations, including personal computers, hand-held devices, multi-processor systems, microprocessor-based or programmable consumer electronics, network PCs, minicomputers, mainframe computers, and the like. The invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

With reference to FIG. 1, an exemplary system for implementing the invention includes a general purpose computing device in the form of a conventional computer 20, including a processing unit 21, a system memory 22, and a system bus 23 that couples various system components including the system memory 22 to the processing unit 21. The system bus 23 may be any of several types of bus structures including a memory bus or memory controller, a peripheral bus, and a local bus using any of a variety of bus architectures. The system memory includes read only memory (ROM) 24 and random access memory (RAM) 25. A basic input/output system (BIOS) 26, containing the basic routines that help transfer information between elements within the computer 20, such as during start-up, may be stored in ROM 24.

The computer 20 may also include a magnetic hard disk drive 27 for reading from and writing to a magnetic hard disk 39, a magnetic disk drive 28 for reading from or writing to a removable magnetic disk 29, and an optical disk drive 30 for reading from or writing to removable optical disk 31 such as a CD-ROM or other optical media. The magnetic hard disk drive 27, magnetic disk drive 28, and optical disk drive 30 are connected to the system bus 23 by a hard disk drive interface 32, a magnetic disk drive-interface 33, and an optical drive interface 34, respectively. The drives and their associated computer-readable media provide nonvolatile storage of computer-executable instructions, data structures, program modules and other data for the computer 20. Although the exemplary environment described herein employs a magnetic hard disk 39, a removable magnetic disk 29 and a removable optical disk 31, other types of computer readable media for storing data can be used, including magnetic cassettes, flash memory cards, digital video disks, Bernoulli cartridges, RAMs, ROMs, and the like.

Program code means comprising one or more program modules may be stored on the hard disk 39, magnetic disk 29, optical disk 31, ROM 24 or RAM 25, including an operating system 35, one or more application programs 36, other program modules 37, and program data 38. A user may enter commands and information into the computer 20 through keyboard 40, pointing device 42, or other input devices (not shown), such as a microphone, joy stick, game pad, satellite dish, scanner, or the like. These and other input devices are often connected to the processing unit 21 through a serial port interface 46 coupled to system bus 23. Alternatively, the input devices may be connected by other interfaces, such as a parallel port, a game port or a universal serial bus (USB). A monitor 47 or another display device is also connected to system bus 23 via an interface, such as video adapter 48. In addition to the monitor, personal computers typically include other peripheral output devices (not shown), such as speakers and printers.

The computer 20 may operate in a networked environment using logical connections to one or more remote computers, such as remote computers 49a and 49b. Remote computers 49a and 49b may each be another personal computer, a server, a router, a network PC, a peer device or other common network node, and typically include many or all of the elements described above relative to the computer 20, although only memory storage devices 50a and 50b and their associated application programs 36a and 36b have been illustrated in FIG. 1. The logical connections depicted in FIG. 1 include a local area network (LAN) 51 and a wide area network (WAN) 52 that are presented here by way of example and not limitation. Such networking environments are commonplace in office-wide or enterprise-wide computer networks, intranets and the Internet.

When used in a LAN networking environment, the computer 20 is connected to the local network 51 through a network interface or adapter 53. When used in a WAN networking environment, the computer 20 may include a modem 54, a wireless link, or other means for establishing communications over the wide area network 52, such as the Internet. The modem 54, which may be internal or external, is connected to the system bus 23 via the serial port interface 46. In a networked environment, program modules depicted relative to the computer 20, or portions thereof, may be stored in the remote memory storage device. It will be appreciated that the network connections shown are exemplary and other means of establishing communications over wide area network 52 may be used.

Figure 2:
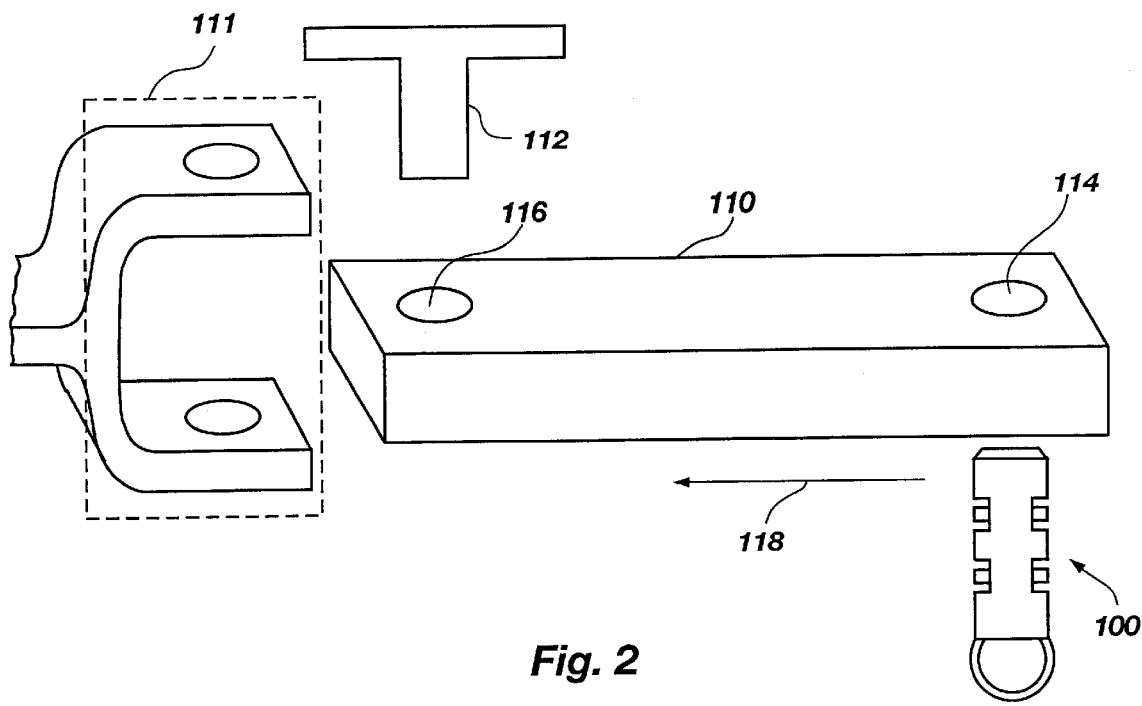
FIG. 2 is a perspective view of a draw bar and illustrates how the draw bar may be connected to both a farm implement using a connection pin and to a tractor using a hitch pin.
Figure 3:
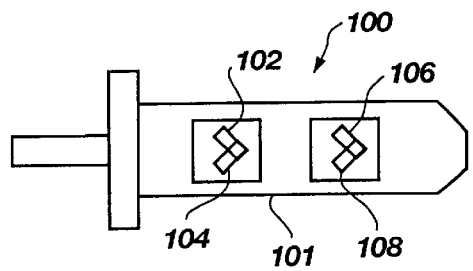
FIG. 3 is a side view of the hitch pin and illustrates an exemplary positioning of the load sensors.
Figure 4:
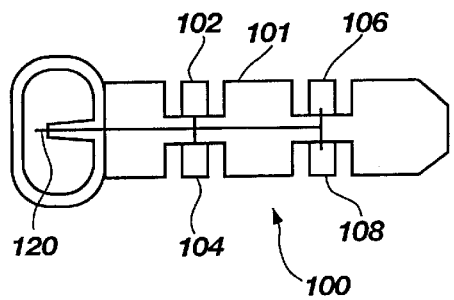
FIG. 4 is a top view of the hitch pin and illustrates an exemplary positioning of load sensors along the shank of the hitch pin.

FIG. 2 is a perspective view of a draw bar, a hitch pin and a connection pin. The draw bar 110 is a metal bar that is typically provided on farm equipment such as tractors. The draw bar 110 enables tractors to attach with and pull farm implements. The draw bar 110 is typically attached to the rear of a tractor by the hitch pin 100. The hitch pin 100, which is described in more detail with reference to FIGS. 3 and 4, is inserted through the opening 114 and into a corresponding opening (not shown) located on the tractor (not shown). After the hitch pin 100 is inserted in this manner, it may be locked into position such that the draw bar 110 may be used to connect with and pull a farm implement.

The draw bar 110, in order to connect with a farm implement, has an opening 116 on the opposite end of the draw bar 110 from the opening 114. The opening 116, in combination with the connection pin 112, is used to attach the draw bar 110 to a farm implement (not shown). To this end, the farm implement has a mechanical arrangement 111 that allows the connection pin 112 and the opening 116 to removably connect the draw bar 110 with the farm implement.

After a farm implement is connected to a tractor via the draw bar 110, the tractor may pull the farm implement. Exemplary farm implements include a plow, a drill, a rake, a drag, a pull behind combine, a planter, a scraper, a disc, a harrow and any other farm implement that may be used in conjunction with a tractor. Because the draw bar 110 is used to pull or push the farm implement, and because the sole connection point between the draw bar 110 and tractor is the hitch pin 100, the force required exerted by the tractor to pull the farm implement is effectively exerted on the hitch pin 100. Stated differently, because the hitch pin 100 is the sole connection between the tractor and the farm implement, the pull force created by the farm implement is exerted on the hitch pin 100. This force is often referred to as a shear force. The draw bar 110 is an example of an attachment device the permits machinery such as tractors to connect with machinery such as farm implements. Other attachment devices include a three point hitch of a tractor and other interfaces that may be secured or connected to the machinery using bolts or pins such as the hitch pin 100.

The hitch pin 100 is an example of pin means for measuring a load or pull force. The pin means also secures the attachment device to the tractor or other machinery. In the case of a draw bar, there is typically a single hitch pin or pin means. In the case of a three point hitch, there are usually three hitch pins, but the pin means is intended to encompass one or more hitch pins. In some instances, the pin means is used to connect the attachment device directly to an implement rather than secure the attachment device to the tractor or other machinery. Further, the term hitch pin is intended to encompass other bolts and pins which may be used to connect machinery to an implement. When the machinery is connected with the implement, the machinery may act on the implement. Examples of acting on the implement include pulling the implement, pushing the implement, causing the implement to execute its function, and the like. For example, when a planter is pulled by a tractor to plant a crop, the tractor is acting on the planter.

As illustrated in FIGS. 3 and 4, the present invention provides an instrumented hitch pin that measures the shear force or pull load of the farm implement. FIG. 3 illustrates a side view of an instrumented hitch pin 100. The hitch pin 100 includes a plurality of load sensors or strain gauges that are strategically placed on a shaft 101 of the hitch pin 100 to measure the pull load. In a preferred embodiment, the hitch pin 100 includes eight load sensors. In FIG. 3, two load sensors are each located at points 102, 104, 106 and 108. The placement of the load sensors on the hitch pin 100 are often dependent on the configuration of the draw bar 110 and the tractor. More specifically, the hitch pin 110 for each separate make of tractor will most likely have the load sensors placed in different locations along the shank of the hitch pin, because hitch pins are usually specific to a tractor. However, the ability to accurately measure the shear force or the pull load is not dependent on the make of the tractor. Rather the load sensors are strategically placed on each separate hitch pin such that accurate measurements of the pull force or shear force may be collected.

FIG. 4 illustrates a side view of the hitch pin 100 that is rotated 90 degrees from the hitch pin 100 illustrated in FIG. 3. As shown, the load sensors at points 102, 104, 106 and 108 are integrated with the hitch pin 100 in a manner that permits the load sensors to accurately measure a load pull or the shear force. Referring to FIG. 2, arrow 118 shows the direction of the pull or shear force when the tractor is pulling a farm implement. It is therefore important to correctly orient the hitch pin I 00 within the opening 114 of the draw bar 110 to ensure that the pull force is accurately measured. The load sensor leads 120 are provided through the hitch pin 100 such that the data provided by the load sensors may be obtained and recorded. Because each separate make and model of tractor will typically be equipped with a hitch pin and draw bar that are different from the hitch pins and draw bars provided with other tractors, the instrumented hitch pin 100 will vary for each separate tractor as previously described. More particularly, the placement of the load sensors may vary in order to optimize the collected data.

Figure 5:
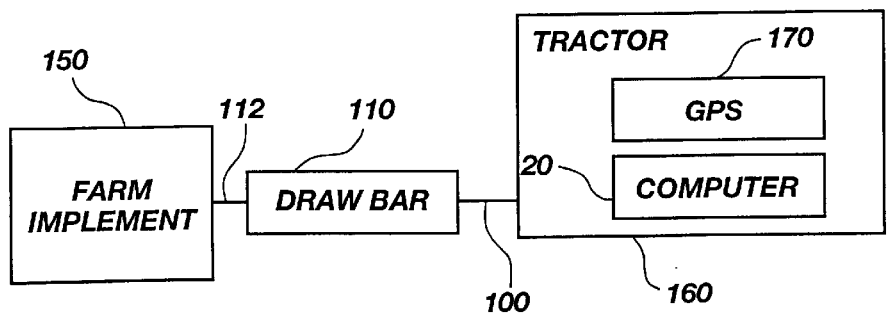
FIG. 5 is a block diagram that illustrates an exemplary system for measuring the physical characteristics of the soil and for generating a spatially variable map of soil's physical characteristics.

FIG. 5 illustrates a block diagram that illustrates a system implementing the systems and methods of the present invention. FIG. 5 illustrates a draw bar 1 10 that is connected with a tractor 160 using a hitch pin 100. The draw bar 110 is also connected with a farm implement 150 using a connection pin 112. As a result, the tractor 160 is capable of pulling the farm implement 150. The force required to pull the farm implement 150 is measured at the hitch pin 100 as described above. Stated another way, the farm implement 150 exerts a load or pull force on the hitch pin, which secures the draw bar 110 to the tractor 160 or other machinery. Referring to the shear force is equivalent to referring to the load force. The load force is the force required to pull the farm implement through or across the soil. As a result, the weight of the farm implement contributes to this force. However, it should be noted that measurements that are strictly attributed to the weight of the farm implement are not necessarily indicative of the physical characteristics of the soil. This type of measurement may occur, for example, when a planter is not engaged in planting a crop but is simply rolling behind the tractor. The force measurements of the hitch pin 100 are provided to the computer 20 or other data acquisition system where they are stored.

FIG. 5 also illustrates a Global Positioning System (GPS) 170. The GPS 170 is used to precisely locate or identify the position of the tractor 160 as a field is traversed. When the shear force or pull load is measured by the hitch pin 100, the computer 20 associates each measured shear force with the position or location provided by the GPS 170 for later analysis. The measurements can be taken continuously or in any interval specified by a user. Preferably, measurements are taken and collected every few feet such that an accurate representation of the physical characteristics of the soil may be obtained from the collected data.

After the field has been traversed and the data from the GPS 170 and the hitch pin 100 has been collected, a map may be generated which represents the spatial variability of the force with respect to the soil. Importantly, this data, which is needed to generate the map, may be collected while other farming operations, such as plowing or planting, are performed. The spatial variability of the force may be used to infer, estimate, or calculate, other physical characteristics of the soil including, but not limited to, density, hardness, water content, and the like. The spatial variability in the soil conditions may be analyzed to have a better understanding of the spatial variability in the crop yield and may also be used to selectively plant, fertilize, water, and till the soil such that crop production is maximized.

Because the data may be collected using a variety of farm implements, it is possible to generate a three dimensional map of the spatial variability of the physical characteristics of the soil. For example, farm implements such as plows dig deep into the soil. As a result, the collected data may correspond to a particular soil depth. A planter, on the other hand does not dig as deep into the soil as a plow and the data collected while pulling a planter may therefore correspond to a different soil depth. Using various farm implements in this manner enables a three dimensional map of the variability of the physical characteristics to be measured and generated.

In another embodiment, the present invention may be used with farm implements that do not penetrate the soil or otherwise create a pull load that is not associated with the weight of the farm implement. In these situations, a probe that penetrates the ground may be fastened to the non-penetrating farm implement such that the necessary data may be collected. In another embodiment, the hitch pin described herein can be used in conjunction with a three point hitch system that is also present on many tractors. In this case, however, the measured force will have to be processed according to how the force is distributed among all of the connections of a three point hitch, which would have three hitch pins that are each measuring a shear force. In the case of a front end loader connected to a tractor with multiple hitch pins, the multiple hitch pins will measure a push force rather than a pull force. The direction is not as important as the magnitude of the force because the spatial variability map is preferably generated using magnitudes as opposed to directions.

In another embodiment of the present invention and because the data is collected in real time, the collected data may be used to make adjustments to the operation of the tractor 160 as well as the farm implement 150 in real time. This can result in more efficient farming operations.

While the present invention has been described in terms of farm related machinery and in the context of a draw bar or other attachment device, the systems and methods of the present invention are not limited to the agricultural or farming equipment described herein. The hitch pin can be integrated with semi-trucks to measure the pull load, where the truck is the machinery and the trailer is the implement that is connected with the machinery. The hitch pin can be integrated with graders to measure the grading force, which is indicative of the physical characteristics of the soil or other surface being graded. The grader is the machinery and the blade of the grader is the implement and the hitch pin is used to connect the blade to the grader such that the force created when earth or other material is graded may be measured and recorded. More generally, the present invention can be adapted to any system using bolted or pinned connections or with connections where a force may be measured. For example, a truck uses a ball to connect with a horse trailer and the ball may be instrumented with load sensors to measure the pull force of the horse trailer. The ball is therefore another example of pin means for measuring a load force.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. In conjunction with a machinery capable of pushing or towing an implement, the implement being connectible with the machinery by way of an attachment device, a system suitable for collecting data concerning various physical characteristics of a soil, the system comprising:
   a hitch pin configured to engage at least one of the attachment device and the implement, said hitch pin comprising:
   a shank defining at least first and second recesses;
   at least a first load sensor and at least a second load sensor, said at least a first load sensor being substantially disposed within said first recess and said at least a second load sensor being substantially disposed within said second recess, and said at least a first load sensor and said at least a second load sensor being arranged in a predetermined spatial relationship with respect to each other; and
   a load sensor lead attached to each of said load sensors;
   a data acquisition module in communication with said load sensors by way of said load sensor leads; and
   a positioning module in communication with said data acquisition module and said load sensors.

2. The system as recited in claim 1, wherein said data acquisition module comprises a computer.

3. The system as recited in claim 1, wherein said positioning module comprises a global positioning system.

4. The system as recited in claim 1, wherein said predetermined spatial relationship is such that said at least a first load sensor and said at least a second load sensor are disposed at an angle of about ninety degrees with respect to each other.

5. The system as recited in claim 1, wherein at least one of said load sensors comprises a strain gauge.

6. A hitch pin suitable for use in facilitating removable attachment of an implement to machinery, wherein the machinery is configured to tow or push the implement, the hitch pin comprising:
   a shank defining at least first and second recesses;
   at least a first load sensor and at least a second load sensor, said at least a first load sensor being substantially disposed within said first recess and said at least a second load sensor being substantially disposed within said second recess, and said at least a first load sensor and said at least a second load sensor being arranged in a predetermined spatial relationship with respect to each other; and
   a load sensor lead attached to each of said load sensors.

7. The hitch pin as recited in claim 6, wherein said predetermined spatial relationship is such that said at least a first load sensor and said at least a second load sensor are disposed at an angle of about ninety degrees with respect to each other.

8. The hitch pin as recited in claim 6, wherein at least one of said load sensors comprises a strain gauge.

9. The hitch pin as recited in claim 6, wherein said shank further defines third and fourth recesses wherein are substantially disposed, respectively, at least a third load sensor and at least a fourth load sensor, said at least a third load sensor and said at least a fourth load sensor pairs arranged in a predetermined spatial relationship with respect to each other.

10. The hitch pin as recited in claim 9, wherein said predetermined spatial relationship between said at least a first load sensor and said at least a second load sensor is substantially the same as said predetermined spatial relationship between said at least a third load sensor and said at least a fourth load sensor.

11. The hitch pin as recited in claim 9, wherein said predetermined spatial relationship between said at least a third load sensor and said at least a fourth load sensor is such that said at least a third load sensor and said at least a fourth load sensor are disposed at an angle of about ninety degrees with respect to each other.

12. In conjunction with machinery and a plurality of farm implements removably connectible to the machinery, the machinery being configured to push or tow farm implements connected to the machinery, a method suitable for collecting data concerning various physical characteristics of a soil, the method comprising:

measuring, throughout a desired area, at least first and second load forces exerted by the soil on at least one of the farm implements, wherein said first load force comprises a load force measured at a first soil depth and said second load force comprises a load force measured at a second soil depth;

determining three dimensional coordinates of each location at which a load force is measured;

recording said load force measurements and said three dimensional coordinates; and correlating at least some load force measurements to at least one physical characteristic of the soil.

13. The method as recited in claim 12, wherein correlating at least some load force measurements to at least one physical characteristic of the soil comprises correlating said at least some fore load measurements to at least one physical characteristic of the soil selected from the group consisting of: hardness, density, and water-holding capacity.

14. The method as recited in claim 12, further comprising adjusting a rate at which load force measurements are made.

15. The method as recited in claim 12, further comprising using said load force measurements and said three dimensional coordinates to generate a three dimensional map depicting spatial variability, within said desired area, of said at least one physical characteristic of the soil.

16. The method as recited in claim 12, wherein said measuring of said load forces occurs substantially continuously.

17. The method as recited in claim 12, further comprising implementing at least one action with respect to the soil based upon said load force measurements and said three dimensional coordinates.

18. The method as recited in claim 17, wherein implementing at least one action comprises implementing an action selected from the group consisting of: planting, fertilizing, watering, and tilling.

19. A system suitable for collecting data concerning various physical characteristics of a soil, the system comprising:

a machinery;

at least one implement removably connectible to said machinery by way of a substantially horizontal draw bar, said substantially horizontal draw bar including at least one opening and sidewalls defining at least one hitch pin connection recess that runs substantially perpendicular to a major plane of said substantially horizontal draw bar;

a hitch pin configured to removably engage said sidewalls of said at least one hitch pin connection recess when inserted therein in a direction substantially perpendicular to said major plane of said substantially horizontal draw bar, said hitch pin comprising:

a shank defining at least first and second recesses;

at least a first load sensor and at least a second load sensor, said at least a first load sensor being substantially disposed within said first recess and said at least a second load sensor being substantially disposed within said second recess, said at least a first load sensor and said at least a second load sensor being arranged in a predetermined spatial relationship with respect to each other; and a load sensor lead attached to each of said load sensors;

a data acquisition module in communication with said load sensors by way of said load sensor leads; and a positioning module in communication with said data acquisition module and said load sensors.

20. The system as recited in claim 19, wherein said at least one hitch pin connection recess is disposed on said substantially horizontal draw bar at a position nearer to a first end thereof than an opposite second nearest to said at least one implement when said at least one implement is removably connected to said substantially horizontal draw bar.

21. The system as recited in claim 19, wherein at least one of said load sensors comprises a strain gauge.

22. The system as recited in claim 19, wherein said at least one implement comprises a farm implement.

23. The system as recited in claim 19, wherein said positioning module comprises a global positioning system.

24. The system as recited in claim 19, wherein said data acquisition module comprises a computer.

25. The system as recited in claim 19, wherein said shank further defines a third recess and a fourth recess wherein are substantially disposed, respectively, at least a third load sensor and at least a fourth load sensor, said third and fourth load sensors being arranged in a predetermined spatial relationship with respect to each other.

26. The system as recited in claim 25, wherein said predetermined spatial relationship between said at least a first load sensor and said at least a second load sensor is substantially the same as said predetermined spatial relationship between said at least a third load sensor and said at least a fourth load sensor.

27. The system as recited in claim 19, wherein said predetermined spatial relationship is such that said at least a first load sensor and said at least a second load sensor are disposed at an angle of about ninety degrees with respect to each other.

28. The system as recited in claim 19, wherein said hitch pin further comprises at least a third load sensor and at least a fourth load sensor, said at least a third load sensor being substantially disposed within said first recess and said at least a fourth load sensor being substantially disposed within said second recess.

* * * * *